(12) United States Patent
Aghassian

(10) Patent No.: US 8,571,680 B2
(45) Date of Patent: Oct. 29, 2013

(54) EXTERNAL CHARGER USABLE WITH AN IMPLANTABLE MEDICAL DEVICE HAVING A PROGRAMMABLE OR TIME-VARYING TEMPERATURE SET POINT

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/661,944

(22) Filed: Oct. 26, 2012

(65) Prior Publication Data

US 2013/0053925 A1 Feb. 28, 2013

Related U.S. Application Data

(63) Continuation of application No. 12/562,694, filed on Sep. 18, 2009, now Pat. No. 8,321,029.

(51) Int. Cl.
*A61N 1/378* (2006.01)

(52) U.S. Cl.
USPC .................. 607/61; 607/60; 607/30; 320/108

(58) Field of Classification Search
USPC .................................................. 320/107–108
See application file for complete search history.

(56) References Cited

U.S. PATENT DOCUMENTS

| | | | |
|---|---|---|---|
| 5,314,453 A | 5/1994 | Jeutter | |
| 5,690,693 A | 11/1997 | Wang et al. | |
| 5,702,431 A | 12/1997 | Wang et al. | |
| 5,749,909 A | 5/1998 | Schroeppel et al. | |
| 6,516,227 B1 | 2/2003 | Meadows et al. | |
| 6,553,263 B1 | 4/2003 | Meadows et al. | |
| 6,850,803 B1 | 2/2005 | Jimenez et al. | |
| 7,200,504 B1 | 4/2007 | Fister | |
| 7,225,032 B2 | 5/2007 | Schmeling et al. | |
| 7,286,880 B2 | 10/2007 | Olson et al. | |
| 7,444,181 B2 | 10/2008 | Shi et al. | |
| 7,496,404 B2 | 2/2009 | Meadows et al. | |
| 7,505,816 B2 | 3/2009 | Schmeling et al. | |

(Continued)

FOREIGN PATENT DOCUMENTS

| | | |
|---|---|---|
| WO | 96/40367 | 12/1996 |
| WO | 98/11942 | 3/1998 |

(Continued)

*Primary Examiner* — Carl H Layno
*Assistant Examiner* — Paula J Stice
(74) *Attorney, Agent, or Firm* — Wong, Cabello, Lutsch, Rutherford & Brucculeri, LLP.

(57) ABSTRACT

An improved external charger for charging the battery within or providing power to an implantable medical device is disclosed. The improved external charger includes circuitry for detecting the temperature of the external charger and for controlling charging to prevent exceeding a maximum temperature. The external charger in some embodiments includes a user interface for allowing a patient to set the external charger's maximum temperature. The user interface can be used to select either constant maximum temperatures, or can allow the user to choose from a number of stored charging programs, which programs can control the maximum temperature to vary over time. Alternatively, a charging program in the external charger can vary the maximum temperature set point automatically. By controlling the maximum temperature of the external charger during charging in these manners, the time needed to charge can be minimized while still ensuring a temperature that is comfortable for that patient.

23 Claims, 17 Drawing Sheets

(56) References Cited

U.S. PATENT DOCUMENTS

| | | |
|---|---|---|
| 7,769,462 B2 | 8/2010 | Meadows et al. |
| 7,774,069 B2 | 8/2010 | Olson et al. |
| 7,945,334 B2 | 5/2011 | Jimenez et al. |
| 7,979,126 B2 | 7/2011 | Payne et al. |
| 8,010,205 B2 | 8/2011 | Rahman et al. |
| 8,170,681 B2 | 5/2012 | Jimenez et al. |
| 8,193,766 B2 | 6/2012 | Rondoni et al. |
| 8,214,042 B2 | 7/2012 | Ozawa et al. |
| 8,244,367 B2 | 8/2012 | Wahlstrand et al. |
| 2007/0060980 A1 | 3/2007 | Strother et al. |
| 2007/0191904 A1 | 8/2007 | Libbus et al. |
| 2008/0027500 A1 | 1/2008 | Chen |
| 2008/0164839 A1* | 7/2008 | Kato et al. .................. 320/108 |
| 2008/0319497 A1 | 12/2008 | Griffith et al. |
| 2009/0069869 A1 | 3/2009 | Stouffer et al. |
| 2009/0118796 A1 | 5/2009 | Chen et al. |
| 2009/0222066 A1 | 9/2009 | Chen et al. |
| 2010/0204756 A1 | 8/2010 | Aghassian |
| 2010/0305663 A1 | 12/2010 | Aghassian |
| 2011/0004278 A1 | 1/2011 | Aghassian et al. |
| 2011/0093048 A1 | 4/2011 | Aghassian |

FOREIGN PATENT DOCUMENTS

| | | |
|---|---|---|
| WO | 01/097908 | 12/2001 |
| WO | 2005/037370 | 4/2005 |
| WO | 2006/119098 | 11/2006 |
| WO | 2009/055203 | 4/2009 |
| WO | 2009/061537 | 5/2009 |
| WO | 2009/134474 | 11/2009 |

* cited by examiner

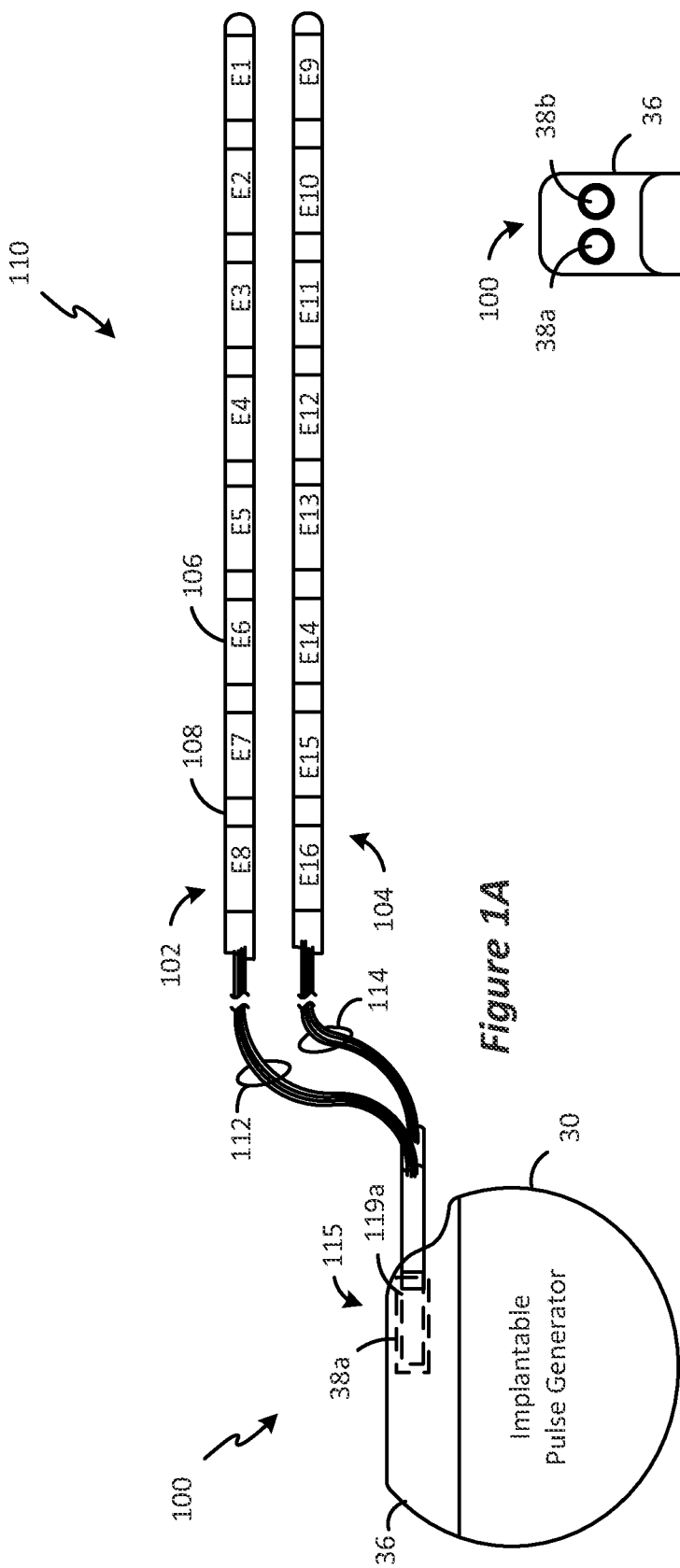
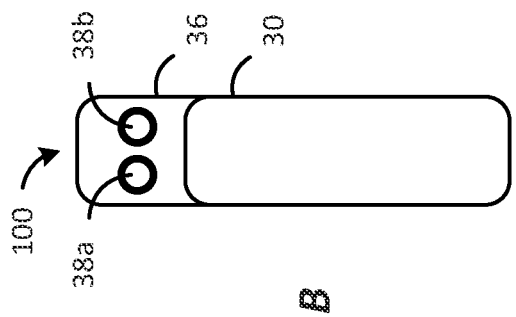

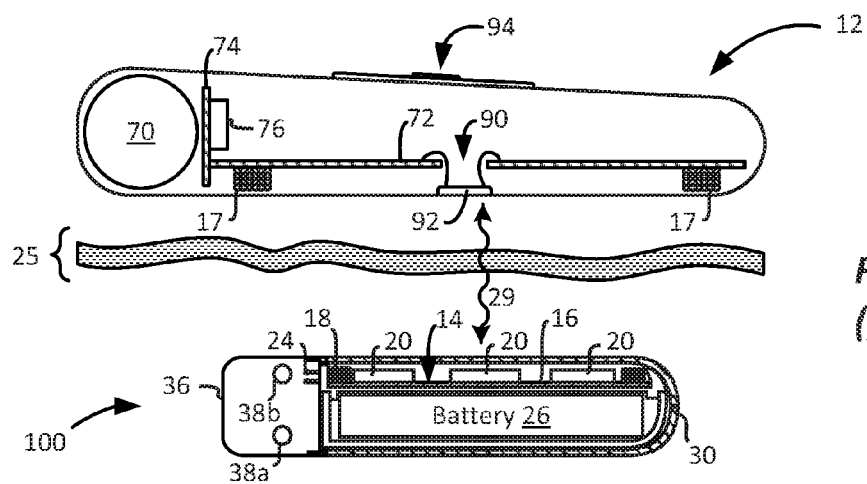
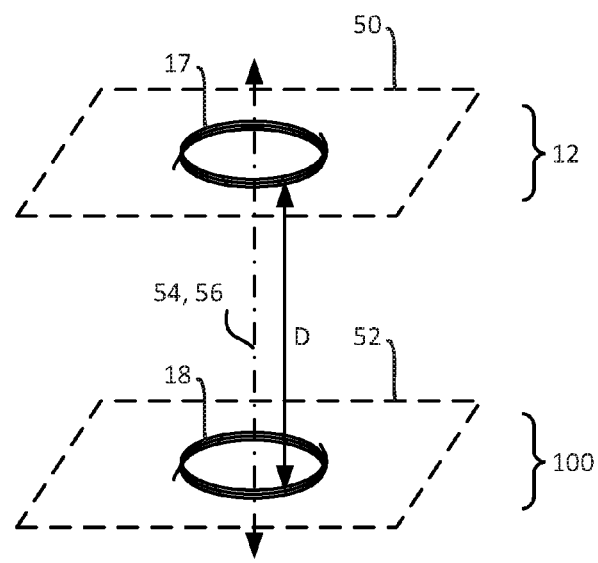
*Figure 2 (prior art)*
*Figure 3 (prior art)*

EXTERNAL CHARGER USABLE WITH AN IMPLANTABLE MEDICAL DEVICE HAVING A PROGRAMMABLE OR TIME-VARYING TEMPERATURE SET POINT

CROSS-REFERENCE TO RELATED APPLICATIONS

This is a continuation of U.S. patent application Ser. No. 12/562,694, filed Sep. 18, 2009, now U.S. Pat. No. 8,321,029 which is incorporated herein by reference in its entirety, and to which priority is claimed.

TECHNICAL FIELD

The present invention relates generally to implantable medical devices, and more particularly, to an external charger for an implantable medical device having programmable temperature regulation.

BACKGROUND ART

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227 ("the '227 patent").

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30. The case 30 usually holds the circuitry and power source or battery necessary for the IPG to function. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112, 114, coupled to each electrode. The signal wires 112 and 114 are connected to the IPG 100 by way of an interface 115, which may be any suitable device that allows the leads 102 and 104 (or a lead extension, not shown) to be removably connected to the IPG 100. Interface 115 may comprise, for example, an electro-mechanical connector arrangement including lead connectors 38a and 38b configured to mate with corresponding connectors 119a and 119b on the leads 102 and 104. In the IPG 100 illustrated in FIG. 1A, there are eight electrodes on lead 102, labeled E1-E8, and eight electrodes on lead 104, labeled E9-E16, although the number of leads and electrodes is application specific and therefore can vary. The electrode array 110 is typically implanted along the dura of the spinal cord, and the IPG 100 generates electrical pulses that are delivered through the electrodes 106 to the nerve fibers within the spinal column. The IPG 100 itself is then typically implanted somewhat distantly in the buttocks of the patient.

As shown in FIG. 2, an IPG 100 typically includes an electronic substrate assembly 14 including a printed circuit board (PCB) 16, along with various electronic components 20, such as microprocessors, integrated circuits, and capacitors, mounted to the PCB 16. Ultimately, the electronic circuitry performs a therapeutic function, such as neurostimulation. A feedthrough assembly 24 routes the various electrode signals from the electronic substrate assembly 14 to the lead connectors 38a, 38b, which are in turn coupled to the leads 102 and 104 (see FIGS. 1A and 1B). The IPG 100 further comprises a header connector 36, which among other things houses the lead connectors 38a, 38b. The IPG 100 can further include a telemetry antenna or coil (not shown), which can be mounted within the header connector 36, for receipt and transmission of data to an external device such as a hand-held or clinician programmer (not shown). As noted earlier, the IPG 100 usually also includes a power source, typically a rechargeable battery 26.

Also shown in FIG. 2 is an external charger 12 that is used to provide power to the IPG 100, which is explained in further detail below. The external charger 12 itself needs power to operate, and therefore may include its own battery 70, which may also be a battery that is rechargeable using a plug-in-the-wall holster ("cradle") or power cord connection much like a cellular telephone. Alternatively, the external charger 12 may lack a battery and instead draw its power directly from being plugged into a wall outlet (not shown). In any event, a primary function of the charger 12, as discussed further below, is to energize a charging coil 17. The external charger 12 can contain one or more circuit boards 72, 74, which contain the circuitry 76 needed to implement such functionality. In a preferred embodiment, and as shown in FIG. 2, most of the circuitry 76 can be located on an orthogonal circuit board 74, which reduces interference and heating that might be produced by the charging coil 17, as is further explained in U.S. Patent Application Publication No. US 2008/0027500.

Further details concerning the structure and function of typical IPGs and IPG systems are disclosed in U.S. Pat. No. 7,444,181.

If the battery 26 in the IPG 100 is rechargeable, it will be necessary to charge the battery 26 periodically using the external charger 12, i.e., a charger that is external to the patient in whom the IPG 100 is implanted. Because the IPG 100 may already be implanted in a patient, wireless recharging is greatly preferred to obviate the need to replace a power-depleted battery 26 via surgery.

To convey energy wirelessly between the external charger 12 and the IPG 100, and as shown in FIG. 2, the charger 12 typically includes an energized alternating current (AC) coil 17 that supplies energy 29 to a similar charging coil 18 located in or on the IPG 100 via inductive coupling. In this regard, the coil 17 within the external charger 12 is wrapped in a plane 50, which lies substantially parallel to the plane 52 of the coil 18 within the IPG 100, as shown schematically in FIG. 3. Such a means of inductive energy transfer can occur transcutaneously, i.e., through the patient's tissue 25. The energy 29 received by the IPG 100's coil 18 can then be rectified and stored in a rechargeable battery 26 within the IPG 100, which in turn powers the electronic circuitry that runs the IPG 100. Alternatively, the energy 29 received can be used to directly power the IPG 100's electronic circuitry, which may lack a battery altogether.

Conventional external chargers 12 typically employ relatively simple user interfaces 94, which simplicity is warranted either because of the relative simplicity of the charging function, or because the external charger 12 may not be visible to the patient while in use, which limits the utility of more complex visual user interfaces. For example, in an SCS application in which the IPG 100 is typically implanted in the buttocks, the external charger 12 is generally behind the patient while charging to align the external charger 12 with the IPG 100. Additionally, the external charger 12 may be covered by clothing while in use, again reducing the utility of a visual user interface. The user interface 94 of the conventional external charger 12 of FIG. 2 therefore typically merely comprises an on/off switch that activates the charger 12, an LED to indicate the status of the on/off switch, and a speaker for emitting a "beep" at various times, such as when the charger is not properly aligned with the IPG 100 or when charging has completed.

Inductive charging between the two coils 17, 18 can produce significant heating in the external charger 12. Such external charger heating could, if unchecked, possibly discomfort or injure the patient. This possibility of injury is heightened because the external charger 12 is often held against the patient's tissue 25 during charging. For example, in an SCS system, the external charger 12 is generally held in place against the buttocks of the patient by a "fanny pack."

Accordingly, prior art external chargers have incorporated temperature monitoring and control circuitry to detect external charger temperatures, and to control charging accordingly. For example, and as shown in FIG. 2, a prior art external charger 12 can include one or more temperature sensors 92, which for example can comprise thermistors or thermocouples affixed by heat conducting epoxy to the housing of the external charger 12. A hole 90 in the circuit board 72 can assist in connecting the temperature sensor 92 to the temperature sensing circuitry (not shown) resident on either of circuit boards 72 or 74. The temperature monitoring and control circuitry generally senses the temperature, T(EC), of the external charger, and in particular sets a maximum temperature, Tmax(EC) for the external charger. The maximum temperature Tmax(EC) may be set to 41° C. (~106° F.) for example, which temperature is conservatively picked by the manufacturer of the external charger 12 as a temperature that should not discomfort or injure a normal healthy adult.

The temperature monitoring and control circuitry in the external charger 12 can operate as illustrated in FIG. 4, which shows the temperature of the external charger, T(EC), during a typical charging session. Initially, the charging circuitry in the external charger 12 is enabled, i.e., an AC current flows through coil 17 in the external charger 12 as previously discussed. As this occurs, T(EC) increases. Eventually, T(EC) equals Tmax(EC). At this point, the temperature sensing circuitry would inform the microcontroller in the external charger 12 to suspend charging, i.e., to cease current flow through coil 17. Once the current ceases, the T(EC) will start to fall. At some point—for example after some time duration or when a minimum T(EC) (Tmin(EC)) is reached as illustrated—charging can be enabled until once again T(EC) reaches Tmax(EC), etc. The result is that charging is duty cycled between enabled and disabled states.

Although the charging scheme illustrated in FIG. 4 ensures that the external charger 12 never exceeds a predefined maximum safe temperature, Tmax(EC), the inventors consider such scheme non-optimal, because it fails to allow for differences between patients, and does not provide any way to control external charger 12 heating characteristics. For example, if a patient is not particularly heat sensitive, that patient may be able to tolerate a higher Tmax(EC), such as 42° C. for example. However, if Tmax(EC) is constrained to 41° C. by the manufacture of the external charger 12, charging will not take place as aggressively as that patient could tolerate: the current in the charging coil 17 would be limited, or charging would be suspended for greater amounts of time. In either case, the result is that charging will be performed too slowly for that patient. This is inconvenient, as patients would generally like charging to occur as quickly as possible. On the other hand, if a patient is unusually heat sensitive for some reason, perhaps because of a medical condition, that patient might be more comfortable with a lower Tmax(EC), say 40° C. for example. In this case, if Tmax(EC) were constrained to 41° C. by the manufacture, that patient would perceive charging as uncomfortably warm.

BRIEF DESCRIPTION OF DRAWINGS

FIGS. 1A and 1B illustrate an implantable pulse generator (IPG), and the manner in which an electrode array is coupled to the IPG in accordance with the prior art;

FIG. 2 illustrates the IPG in relation to an external charger in accordance with the prior art;

FIG. 3 illustrates the relationship of the charging coils in the external charger and in the IPG during charging in accordance with the prior art;

DESCRIPTION OF EMBODIMENTS

An improved external charger for charging the battery within or providing power to an implantable medical device is disclosed. The improved external charger includes circuitry for detecting the temperature on the portion of the external charger that is applied to the patient and for controlling charging to prevent a maximum temperature from being exceeded. The external charger in some embodiments includes a user interface for allowing a patient to set the maximum temperature for the external charger. The user interface can be used to select either constant maximum temperatures, or can allow the user to choose from a number of charging programs, which programs can control the maximum temperature to vary over time. Alternatively, a charging program in the external charger can vary the maximum temperature set point automatically. By controlling the maximum temperature of the external charger during charging in these manners, the time needed to charge can be minimized while still ensuring a temperature that is comfortable for that patient.

The disclosed embodiments are not limited to use with an implantable pulse generator (IPG) system, but more generically are usable with any implantable medical device system in which an implanted medical device benefits or requires wireless charging from an external source. For example, the disclosed embodiments may be used as part of a system involving a pacemaker, defibrillator, cochlear stimulator, retinal stimulator, a stimulator configured to produce coordinated limb movement, a cortical and deep brain stimulator, or in any other neural stimulator system configured to treat urinary incontinence, sleep apnea, shoulder sublaxation, etc. The disclosed embodiments may also be used as part of a system in which the implanted medical device comprises a sensor or an active device not involving electrical stimulation (e.g., a drug pump).

Figure 4:
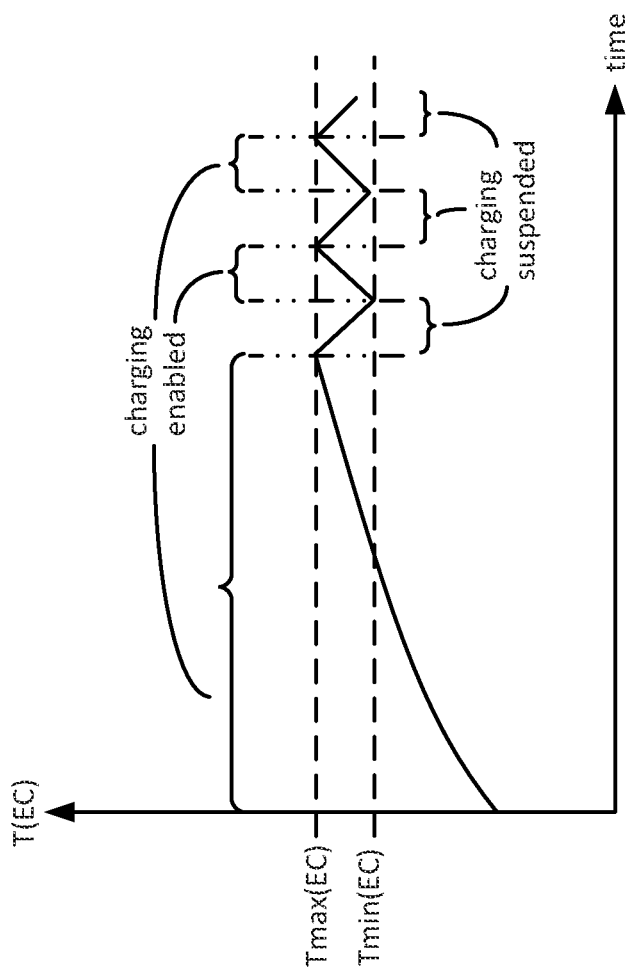
FIG. 4 illustrates regulation of the external charger's temperature during IPG battery charging in accordance with the prior art.
Figure 5B:
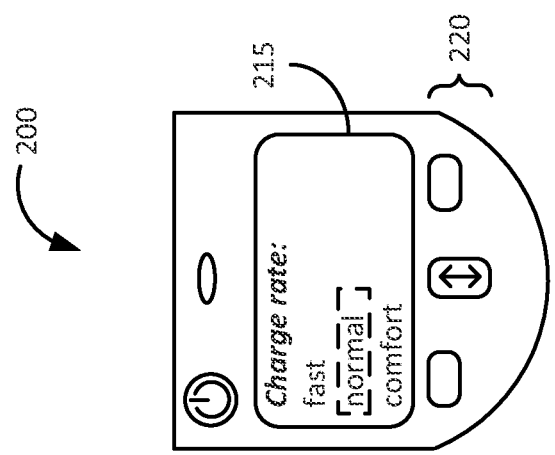
FIGS. 5A and 5B illustrate two embodiments of an improved external charger that allow adjustment of temperature settings for the external charger.
Figure 5A:
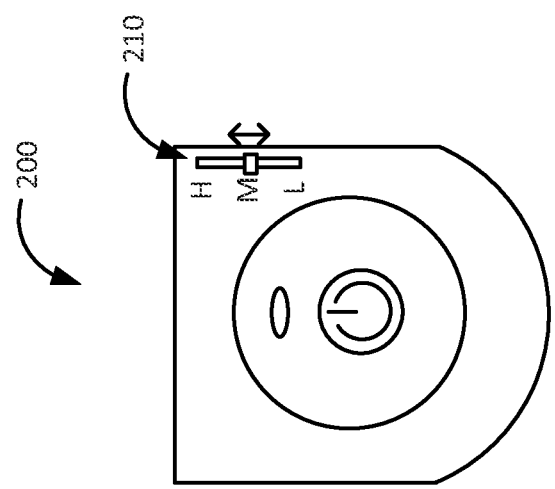

FIGS. 5A and 5B illustrate two embodiments of an external charger 200 that allows adjustment of maximum temperature set point (Tmax(EC)) for the external charger 200. In the embodiment of FIG. 5A, a slide switch 210 user interface allows the patient to switch the external charger 200 between Fast, Normal, and Comfort settings (denoted as H, M, and L respectively in FIG. 5A). FIG. 5B provides a different user interface, including a display 215 and buttons for allowing a "charge Rate" to be selected. Although indicated to the user as an "Rate" setting, the reality underlying the setting is an adjustment to Tmax(EC) (and possibly also an adjustment to Tmin(EC)). Of course, text accompanying the user interfaces could also reference "temperature" if that would be more intuitive to the patient, and could even reference the actual settings for Tmax(EC) (e.g., "42° C.," "41° C.," "40° C."). Although not illustrated in FIG. 5B, the user interface might alternatively allow the patient to increment or decrement the charging intensity/temperature setting (e.g., in 0.5° C. increments) without having the patient choose an absolute setting. Although three settings are shown in FIGS. 5A, 5B, other numbers of settings can be provided and designated in any way desirable. Additionally, other user interfaces can be used beyond those depicted for selecting the maximum temperature, and no particular user interface is important to the implementation.

Figure 6:
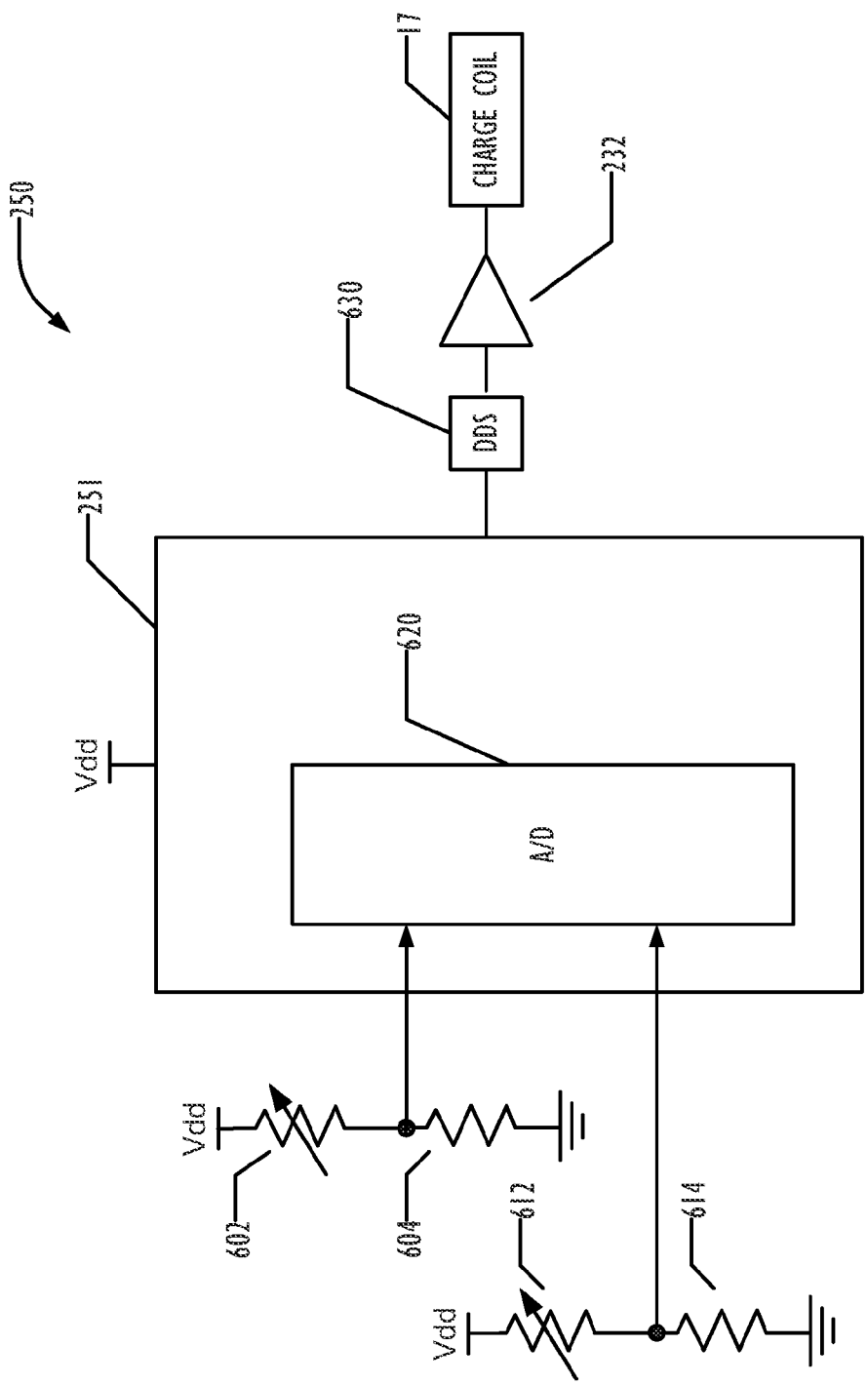
FIG. 6 illustrates temperature monitoring and control circuitry for one embodiment of the external chargers of FIGS. 5A and 5B.

FIG. 6 illustrates an embodiment of a temperature monitoring and control circuitry 250 useable in the external charger 200 of FIGS. 5A and 5B. By way of overview, temperature monitoring and control circuitry 250 operates to sense the temperature, T(EC), of the applied portion of the external charger 200, and to control the temperature between Tmax(EC) and Tmin(EC) by selectivity enabling or disabling the charging coil 17 during charging. In this embodiment, two thermistors 602, 612 allow monitoring the temperature of more than one portion of the external charger 200, biased by resistors 604, 614. Although two thermistors 602, 614 are illustrated in FIG. 6, the number of thermistors is illustrative only and any number of thermistors can be employed to monitor as many portions of the external charger 200 as desired.

The voltages produced by thermistors 602,604 are converted to digital values by an analog to digital logic 620 of the microcontroller 251. The logic 620 can be incorporated into the microcontroller 251 as illustrated, or can be a separate logic external to the microcontroller as desired. The Tmax (EC) and Tmin(EC) values are then stored by the microcontroller 251, in any desired manner, such as in a memory (not shown) or in registers of the microcontroller 251. If the digitized voltage from thermistors 602, 612 exceeds Tmax(EC), then firmware in the microcontroller 251 can disable the charging coil 17 or reduce the charging rate. Similarly, if the digitized voltage from thermistors 602,612 is less than Tmin (EC), then the firmware can enable the charging coil 17 or increase the charging rate. Direct digital synthesis logic 630 and amplifier logic 232 can be used to control the charging coil 17 by the microcontroller 251.

Figure 6A:
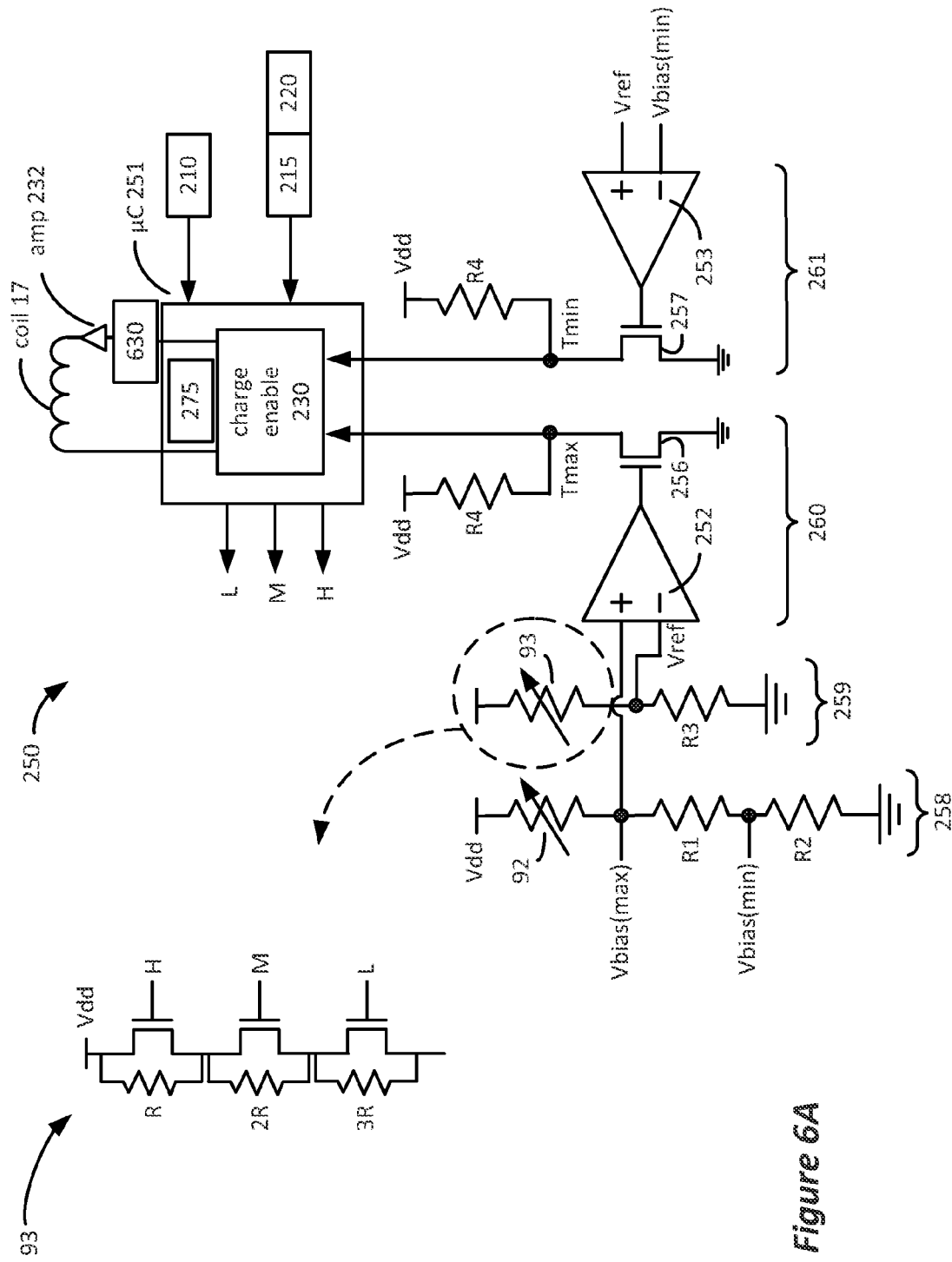
FIG. 6A illustrates temperature monitoring and control circuitry for another embodiment of the external chargers of FIGS. 5A and 5B.

FIG. 6A illustrates another embodiment of a temperature monitoring and control circuitry 250 useable in the external charger 200 of FIGS. 5A and 5B. By way of overview, temperature monitoring and control circuitry 250 operates to sense the temperature, T(EC), of the applied portion of the external charger 200, and to control the temperature between Tmax(EC) and Tmin(EC) by selectivity enabling or disabling the charging coil 17 during charging. In the circuit of FIG. 6A, Tmax(EC) and Tmin(EC) are offset by a predetermined amount, and so the patient's selection at the user interface of a particular charging rate/temperature acts to set both Tmax (EC) and Tmin(EC). However, this is not strictly necessary, and in other circuit implementations, Tmax(EC) and Tmin (EC) can each be separately selected by the patient, or only Tmax(EC) can be selected with Tmin(EC) being preset and not selectable. However, temperature monitoring and control circuits implementing such variations are not shown for simplicity, but, as one skilled in the art will appreciate, would be easily implemented given the circuitry details that follow.

The patient uses the user interface (either slide switch 210, or display/buttons 215/220 for example), to input a charging rate/temperature. This indication is sent to the external charger 200's microcontroller 251, which in turn generates an associated control signal, such as L, M, or H (which, for ease of illustration, matches the low, medium, and high user interface selections in FIG. 5A). These control signals are in turn sent to a variable resistive network 93, whose functionality will be described further below.

Temperature monitoring and control circuitry 250 further comprises two voltage dividers 258 and 259, a Tmax control circuit 260, and a Tmin control circuit 261. Voltage divider 258 includes thermistor 92 (see FIG. 2), and two resistors R1 and R2. These elements, in conjunction with the external charger 200's battery voltage (Vdd), generate two control signals: Vbias(max), which is sent to Tmax control circuit 260, and Vbias(min), which is sent to Tmin control circuit 261. Voltage divider 259 includes the variable resistive network 93 and resistor R3, which elements generate a reference voltage, Vref, which is sent to both control circuits 260 and 261. As will be discussed further below, the relationship between Vbias(max) and Vref sets Tmax(EC), while the relationship between Vbias(min) and Vref sets Tmin(EC). These Tmax(EC) and Tmin(EC) temperatures are by default set by the various resistors to safe values that will not injure or cause discomfort to most patients.

Tmax control circuit 260 comprises a comparator 252 for receiving Vbias(max) and Vref, a transistor 252, and a pull up resistor R4. If Vbias(max)>Vref, comparator 252 output a logic 1, which turns on the transistor 256. This overcomes the effect of pull up resistor R4, and thus pulls control signal Tmax to a logic 0. By contrast, if Vbias(max)<Vref, then transistor 256 is off, and Tmax is pulled to a logic 1 by the pull up resistor R4. Generally speaking, Tmax indicates to the microcontroller 251 whether to enable charging (Tmax=0) or disable charging (Tmax=1), as will be discussed further below. Tmin control circuitry 261 is constructed and operates similarly to the Tmax control circuit 260, and thus such details are not reiterated.

At the onset of charging, and before the external charger 200 has had time to heat up, Vbias(max) is set to be greater than Vref. As just discussed, this sets a condition Tmax=0, which indicates to charge enable circuitry 230 associated with microcontroller 251 that charging can be enabled, i.e., that current can flow through coil 17. Charge enable circuit 230 is shown as part of the microcontroller 251, but it can be separate therefrom. As T(EC) increases during charging, the resistance of thermistor 92 increases, causing the Vbias(max) voltage to decrease. When the temperature T(EC) reaches Tmax(EC), Vbias(max) becomes less than Vref, which sets Tmax=1. This indicates to the charge enable circuitry 230 that Tmax(EC) has been reached, and therefore that charging should be disabled. Rising edges of the Tmax may be latched in the charge enable circuit 230 to ensure that the coil 17 remains disabled, and does not become enabled as soon as the external charger 200 cools to slightly below Tmax(EC), which would set the Tmax line to a logic 0 again.

Once charging is disabled and the external charger 200 begins to cool, it will eventually be suitable to enable charging once again, and such is the function of Tmin control circuit 261. In Tmin control circuit 261, a comparator 253 compares Vref and Vbias(min). Initially, i.e., once cooling begins, Vref>Vbias(min), comparator 253 outputs a logic 1, and the Tmin control signals is drawn to 0 by transistor 257, indicating that charging should not be enabled. As T(EC) continues to fall, the resistance of the thermistor 92 decreases, and Vbias(min) increases. Eventually, when T(EC) reaches Tmin(EC), Vbias(min)>Vref, causing comparator 253 to output a logic 0, which sets Tmin=1. This indicates to charge enable circuitry 230 that Tmin(EC) has been reached, and therefore that charging should once again be enabled. As with Tmax, only rising edges of control signal Tmin are latched at the charge enable circuit 230, avoiding disabling charging of the coil 17 as soon as the temperature T(EC) rises slightly above Tmin(EC).

The default setting of Tmax(EC) in one embodiment is set to 41° C. while Tmin(EC) is set to 39° C., although these values can be tailored to suit a particular implementation. As one skilled in the art will realize, setting such default values can be achieved through setting the varying resistances in the voltage dividers 258 and 259, which is a matter of routine design. The default values in one embodiment can be set at a medium charging intensity/temperature, i.e., when M=1.

Adjustment to Tmax(EC) (and Tmin(EC) in the illustrated example of temperature monitoring and control circuitry 250) occurs via control signals L, M, and H, which as noted above result from the patient's charging intensity/temperature selection at the user interface of the external charger 200. The goal of these control signals is to affect Vref by affecting the resistance of the variable resistive network 93 in voltage divider 259. In this regard, both Tmax(EC) and Tmin(EC) are raised when Vref is lowered, i.e., when the resistance of the variable resistive network 93 is raised. Conversely, Tmax (EC) and Tmin(EC) are lowered when Vref is raised, i.e., when the resistance of the variable resistive network 93 is lowered.

An example variable resistive network 93 for achieving such functionality is shown in FIG. 6A, which comprises three resistors of resistance R, 2R, and 3R respectively gated by the H, M, and L control signals. When the patient selects the H setting, a transistor shorts out resistor R, and the variable resistive network 93's total resistance is 2R+3R=5R, a relatively high resistance which results in a lower Vref, and thus a higher Tmax(EC)/Tmin(EC). When the patient selects the M setting, resistor 2R is shorted, providing a total resistance of R+3R=4R, which smaller resistance ultimately lowers Tmax(EC)/Tmin(EC). When the patient selects the L setting, resistor 3R is shorted, providing an even smaller resistance of R+2R=3R, which lowers Tmax(EC)/Tmin(EC) even further. However, it should be noted that the illustrated resistive network 93, and its control signals, are merely examples, and that other circuits and control signals could be used. Moreover, other techniques not involving restive networks can be used to affect Vref, and hence Tmax(EC) and Tmin(EC). For example, a patient's charging intensity/temperature selection at the user interface can be stored and used to set the output voltage of a bandgap reference voltage generator. Such an embodiment would dispense with the need for a voltage divider 259.

Once Tmax(EC) has been set by the user, it is preferably stored in a non-volatile temperature-parameter memory 275 in the external charger 200 (FIG. 6A), which memory may be located in the microcontroller 251 or external to the microcontroller 251.

Figure 7:
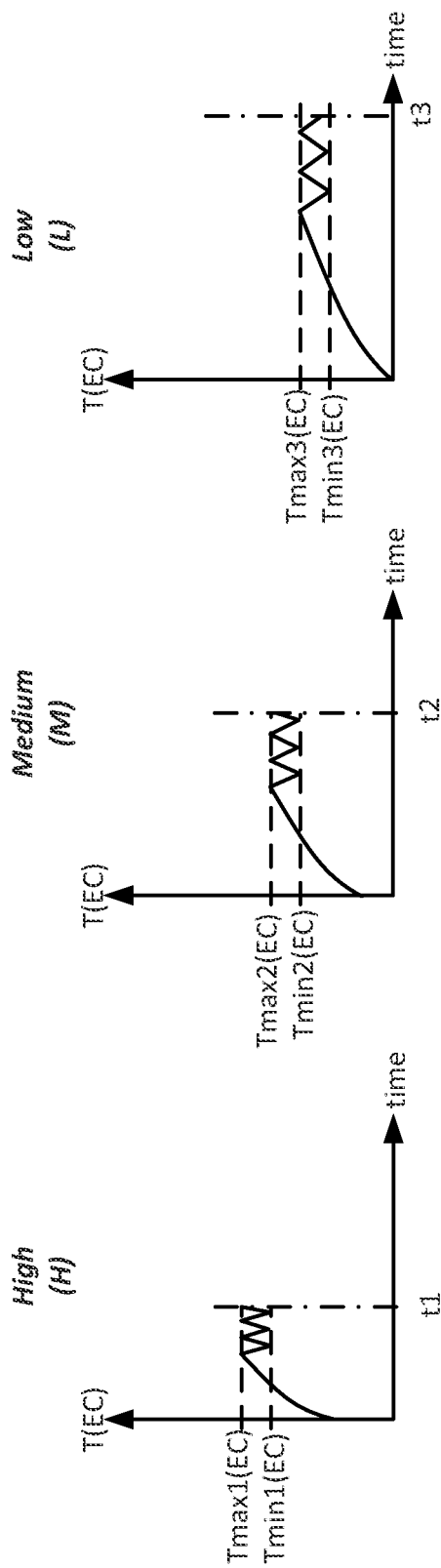
FIG. 7 illustrates regulation of the external charger's temperature during IPG battery charging in accordance with the embodiment illustrated in FIG. 6A.

FIG. 7 illustrates operation of the temperature monitoring and control circuitry 250 of FIG. 6A for the patient-selected charging intensities/temperatures of high, medium, and low (H, M, and L). As illustrated in each of the graphs, the external temperature T(EC) rises from its initial state to Tmax(EC) then oscillates between Tmax(EC) and Tmin(EC) for the remainder of the charging session. Note that the maximum temperature set points decrease with the patient selected setting (Tmax1(EC)>Tmax2(EC)>Tmax3(EC)). (The Tmin (EC) sets points also decrease in this embodiment, but as noted earlier that is not strictly necessary). Moreover, note that higher Tmax values reduce the time necessary to complete charging (t1<t2<t3). This is understandable, because a higher permissible temperature will allow for a higher power output from the external charger 200 (e.g., a higher current in coil 17), which in turn reduces the time necessary to charge the battery 26 in the IPG 100 (see FIG. 2). As a result, charging can be optimized for each particular patient: i.e., a Tmax(EC) can be chosen which is small enough to be comfortable, but larger enough so that the time necessary to charge is minimized.

Figure 8:
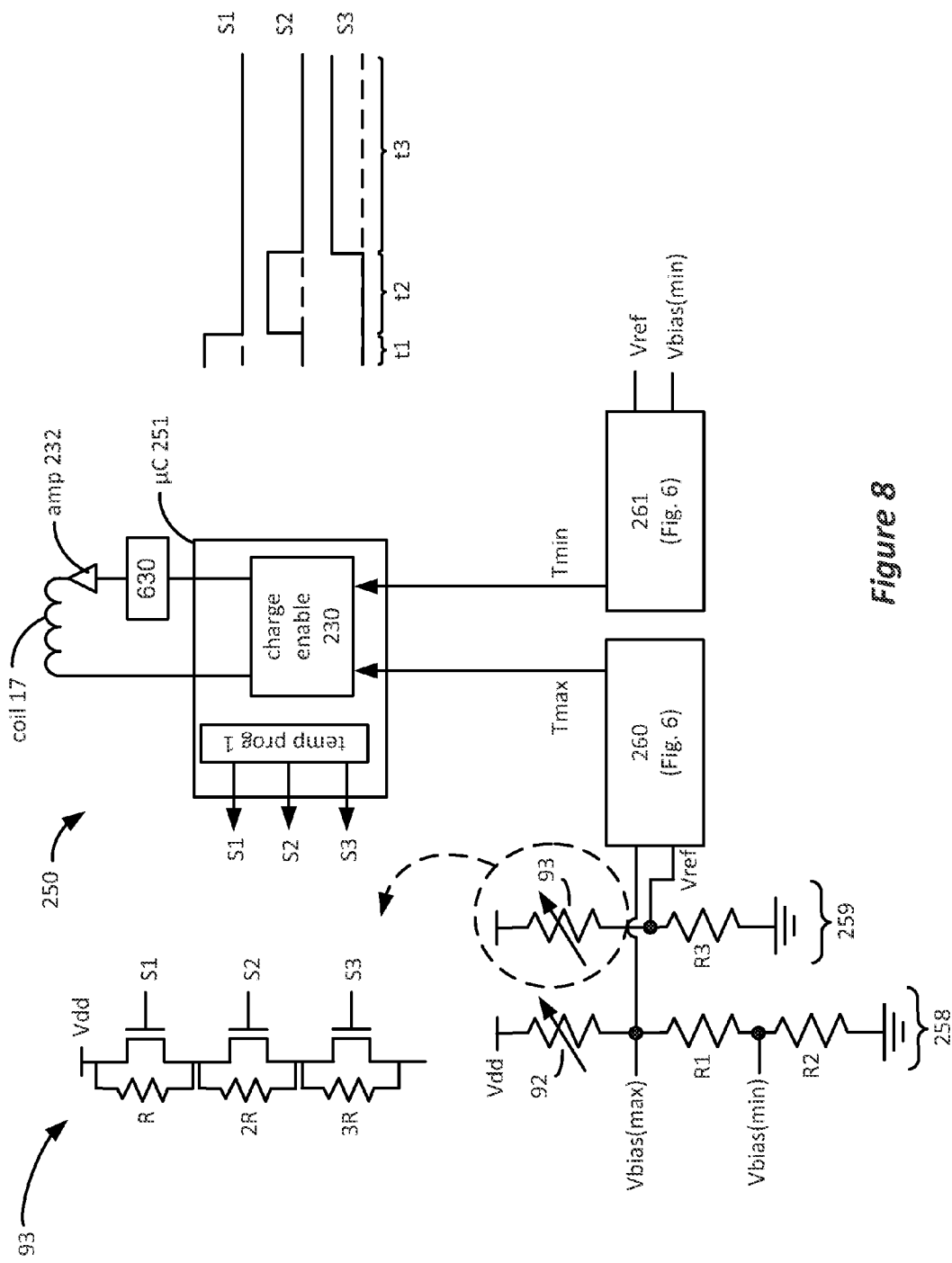
FIG. 8 illustrates temperature monitoring and control circuitry for an external charger having a stored time-varying charging temperature program.

In another embodiment illustrated in FIG. 8, the external charger 200 varies Tmax(EC) (and again in this example, Tmin(EC)) over time. This occurs not by a patient selection at the user interface but instead by automatically executing a temperature program ("temp prog 1") at the microcontroller 251 upon initiating a charging session.

Figure 9:
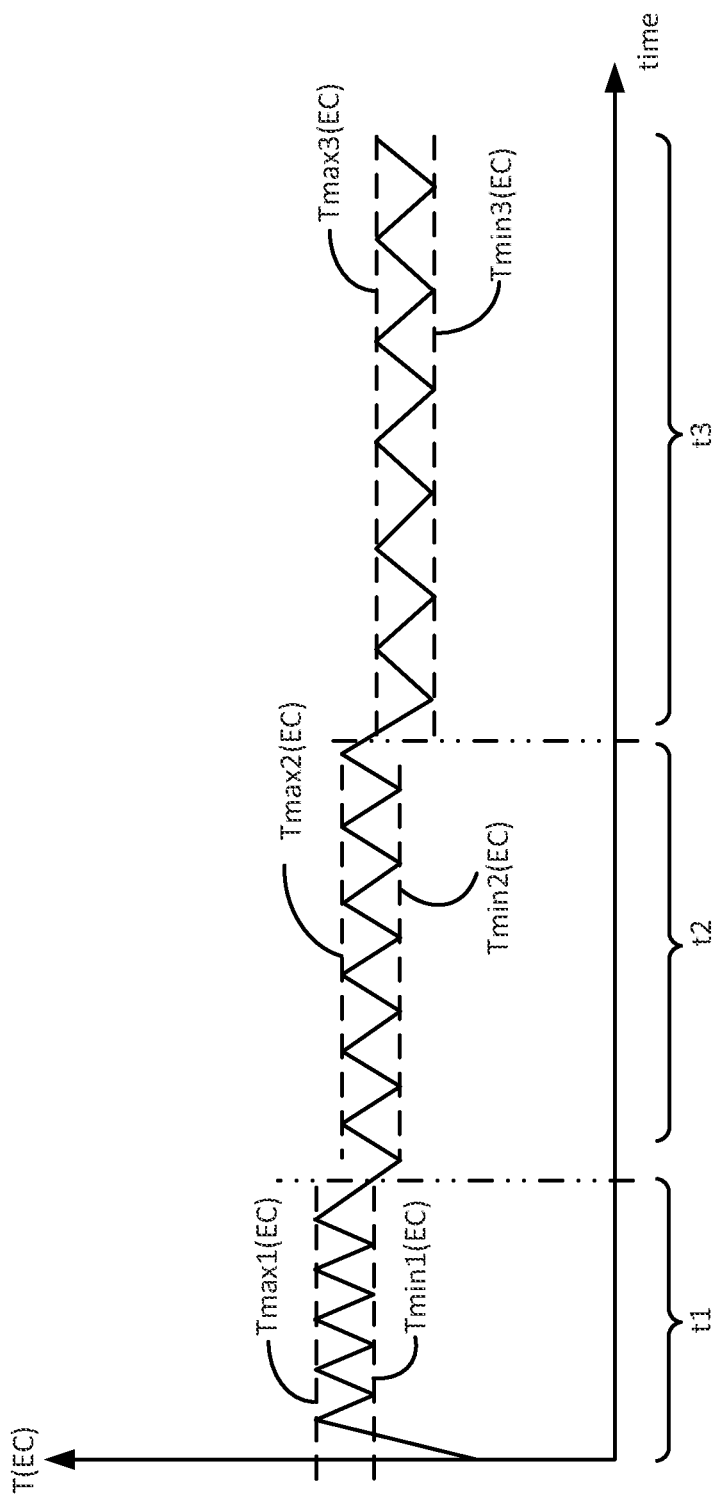
FIG. 9 illustrates regulation of the external charger's temperature during IPG battery charging in accordance with the embodiment illustrated in FIG. 8.

The stored temperature program outputs control signals S1-S3 at particular times, as shown to the right on FIG. 8. In the illustrated example, the temperature program asserts a control signal S1 for a time t1, followed by control signal S2 for a time t2, and followed by control signal S3 for a time t3. The S1, S2, and S3 control signals control the variable resistive network 93 similarly to the H, M, and L control signals of FIG. 6A. Thus, and as shown in FIG. 9, control signals S1-S3 set a high maximum temperature set point (Tmax1(EC)) during t1, a medium Tmax2(EC) during time t2, and a low Tmax3(EC) during time t3. (Again, the corresponding minimum temperatures Tmin1(EC)-Tmin3(EC) are also decreased, but this is not strictly necessary).

This variable-temperature program is logical from consideration of heat loading and comfort of the patient's tissue. Initially, the program chooses a high Tmax1(EC) on the assumption that the patient's tissue has not yet been subject to any heat, and therefore can probably tolerate relatively intense heat from the external charger 200 for at least a short while (t1). During this short while, charging of the IPG's battery would be beneficially accelerated. As the tissue heats up, the patient may eventually no longer tolerate the relative high maximum temperature of Tmax1(EC). Therefore, the maximum temperature is decreased to Tmax2(EC) for a time t2. Although this lower temperature would tend to reduce discomfort, it would also length the time necessary to charge the IPG's battery, and therefore t2 may be greater than t1 as shown (although this is not strictly necessary). For the same reasons, the maximum temperature can again be reduced to Tmax3(EC), although again this may lengthen the time necessary to charge (i.e., t3>t2>t1).

The parameters of the temperature program (i.e., Tmax(EC)-Tmax3(EC), t1-t3) could be specified and stored by the manufacture of the external charger 200. Alternatively, such parameters could be defined and stored by the patient after manufacture using the external charger's user interface. Although the temperature program could be implemented in microcode resident in the external charger's microcontroller 251, it could also easily be implemented using discrete circuitry components as one skilled in the art having benefit of this disclosure will appreciate.

Figure 10:
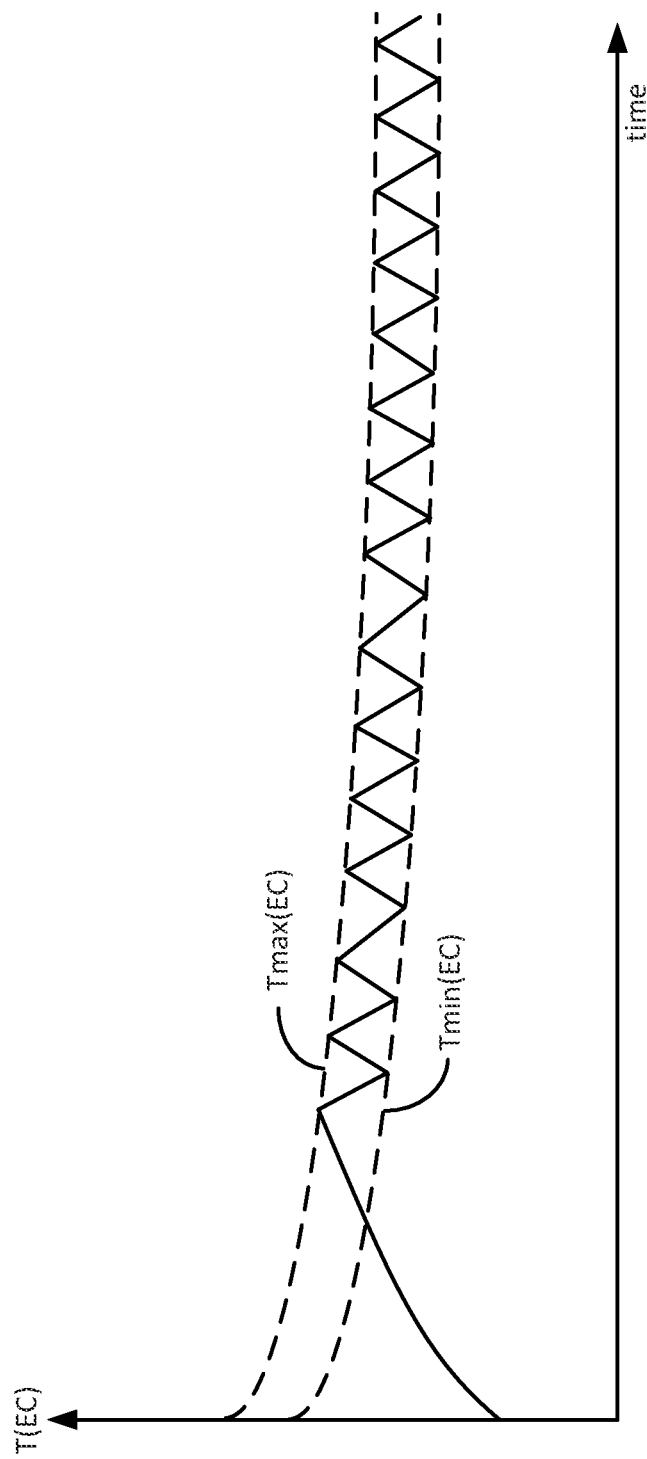
FIG. 10 illustrates another example of regulation of the external charger's temperature during IPG battery charging in accordance with the embodiment illustrated in FIG. 6A.

Although FIG. 9 illustrates a temperature program that varies the charging intensity/temperate in discrete intervals, other temperature programs executable at the microcontroller 251 can effect a smooth variance of Tmax(EC) (and Tmin(EC)), as shown in FIG. 10. Such smoothness can be achieved in many ways, again as one skill in the art having benefit of this disclosure will appreciate.

Figure 11:
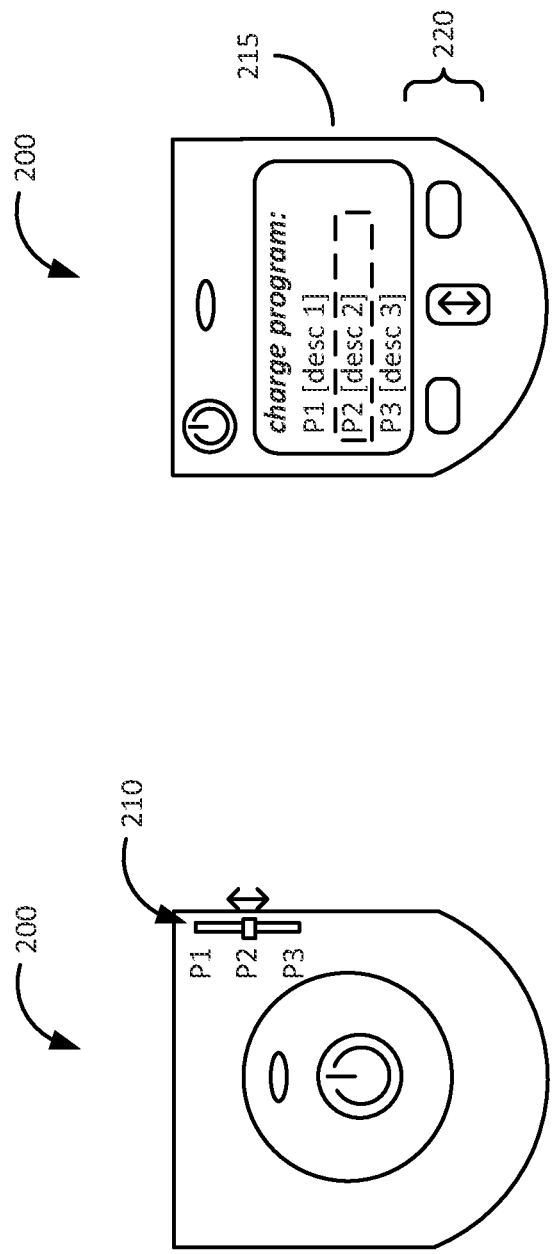
FIGS. 11A and 11B illustrate two embodiments of an improved external charger that allow the patient to select between multiple charging temperature programs.

FIGS. 11A and 11B illustrate examples of an improved external charger 200 in which the patient can select one of a plurality of predefined external charger temperature programs, each of which varies Tmax(EC) in different ways. Similar to an earlier example (see FIGS. 5A and 5B), the user interface can employ a simple slide switch 210 or a display/buttons 215/220 to select between the temperature programs P1, P2, and P3. As illustrated in FIG. 11B, the display 215 may provide a description of each program ("[desc n]") to inform the patient about the basic features of the programs so that the user can make a meaningful selection. As before, the illustrated user interfaces are not mandatory, and other forms could be used.

Figure 12:
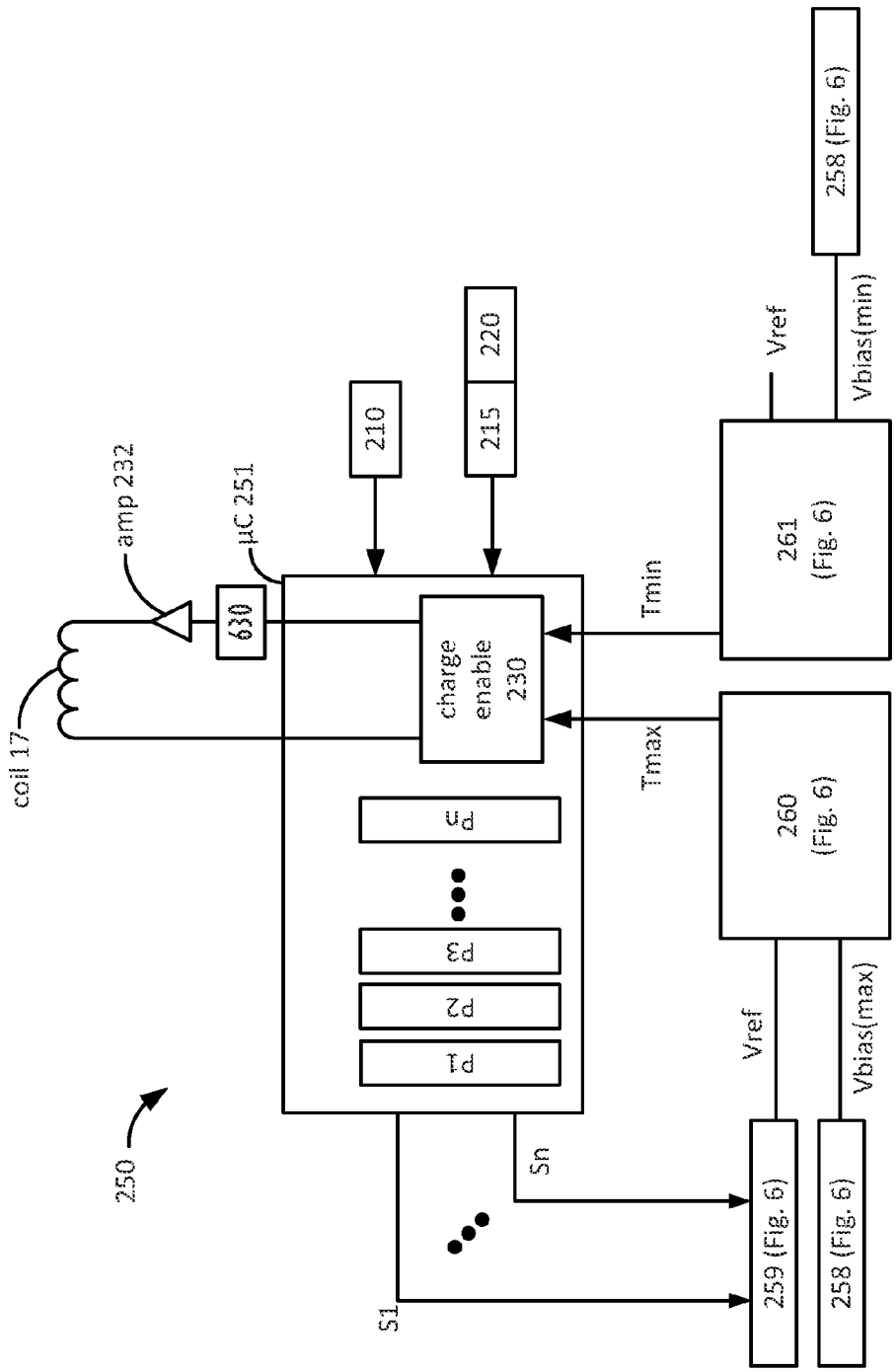
FIG. 12 illustrates a schematic of the temperature monitoring and control circuitry for the external chargers of FIGS. 11A and 11B.

FIG. 12 illustrates the temperature monitoring and control circuitry 250 for the external chargers 200 of FIGS. 11A and 11B. Many of the elements depicted in FIG. 12 were discussed in previous embodiments, and such details are not repeated here. However, of particular note to this embodiment, a plurality of temperature programs (P1-Pn) are stored for execution by the microcontroller 251. As with the embodiment of FIG. 8, execution of a given program results in the issuance of a plurality of control signals S1-Sn. Consistent with earlier examples, the control signals are sent to voltage divider 259 to affect its resistance, which ultimately affects Vref, and hence affects (at least) Tmax(EC). However, as before, a voltage divider 259 is not strictly needed; for example, the control signals S1-Sn could be sent to a bandgap reference voltage generator 259 instead.

Figure 13:
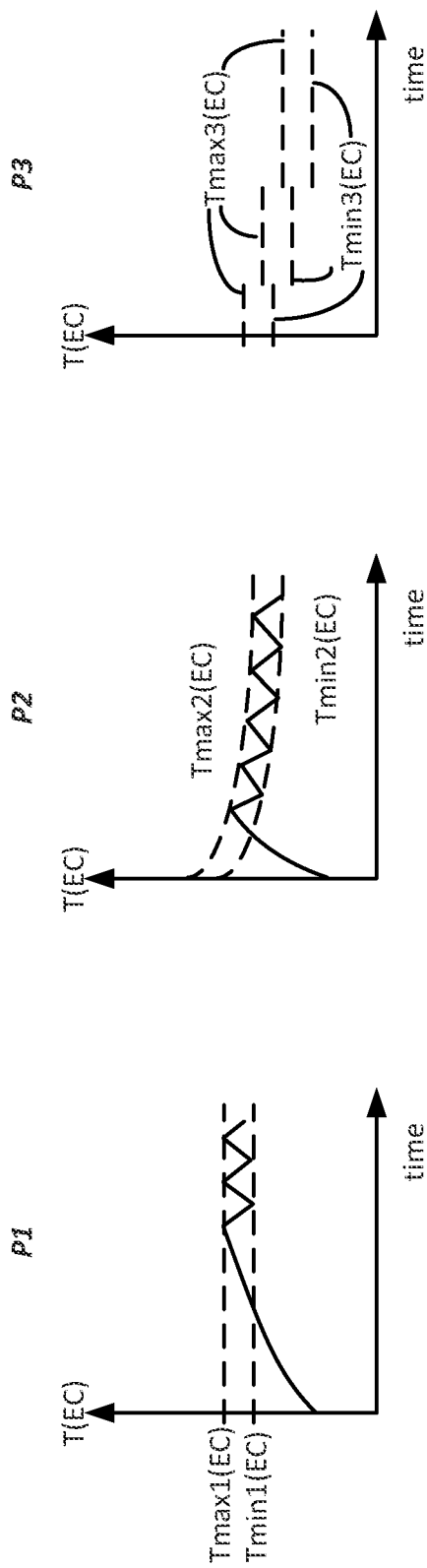
FIG. 13 illustrates regulation of the external charger's temperature during IPG battery charging in accordance with the embodiments illustrated in FIGS. 11A and 11B.

To illustrate operation of the circuit 250 of FIG. 12, assume the patient can choose between three temperature programs as illustrated in FIG. 13, each of which sets the Tmax(EC)/Tmin(EC) values differently. In a first example program (P1), the external charger 200 sets the Tmax1(EC) value to 41° C. and the Tmin1(EC) value to 39° C., and charges using that temperature range for the entire charging session. In a second example program (P2), the external charger 200 initially sets Tmax2(EC) to 43° C. and Tmin2(EC) to 41° C., then continuously decreases those values over time. In a third example program (P3), the external charger 200 initially sets the Tmax3(EC)/Tmin3(EC) values at 40° C./38° C. for the first five minutes, then lowers them to 38° C./36° C. for the next ten minutes, and finally to 37° C./35° C. for the remainder of the charging session.

Although the above-described embodiments allow for adjustment of the Tmax(EC) and Tmin(EC) temperature settings together, other embodiments may allow separate control over each setting as previously noted, or may allow control only over Tmax(EC). Still other embodiments do not require the use of a Tmin(EC) at all, such as with the temperature monitoring and control circuitry 250 of FIG. 14. In this embodiment, the Tmax(EC) and Tmin(EC) temperature values are effectively combined into a single Tset(EC) value. Similarly to the embodiment of FIG. 6A, voltage dividers 258 and 259 in conjunction with Tset control circuitry 282 derive a control signal Tset, which signal is sent to the charge enable circuitry 230. Here, Tset is latched on both rising and falling edges at the charge enable circuitry 230, and thus will oscillate between a logic 1 when T(EC)>Tset(EC), which will disable charging, and a logic 0 when T(EC)<Tset, which will enable charging. To prevent the circuit 250 from switching too quickly between the enabled and disabled states, the charge enable circuitry can employ any of a number of digital filtering or digital integration techniques.

Figure 14:
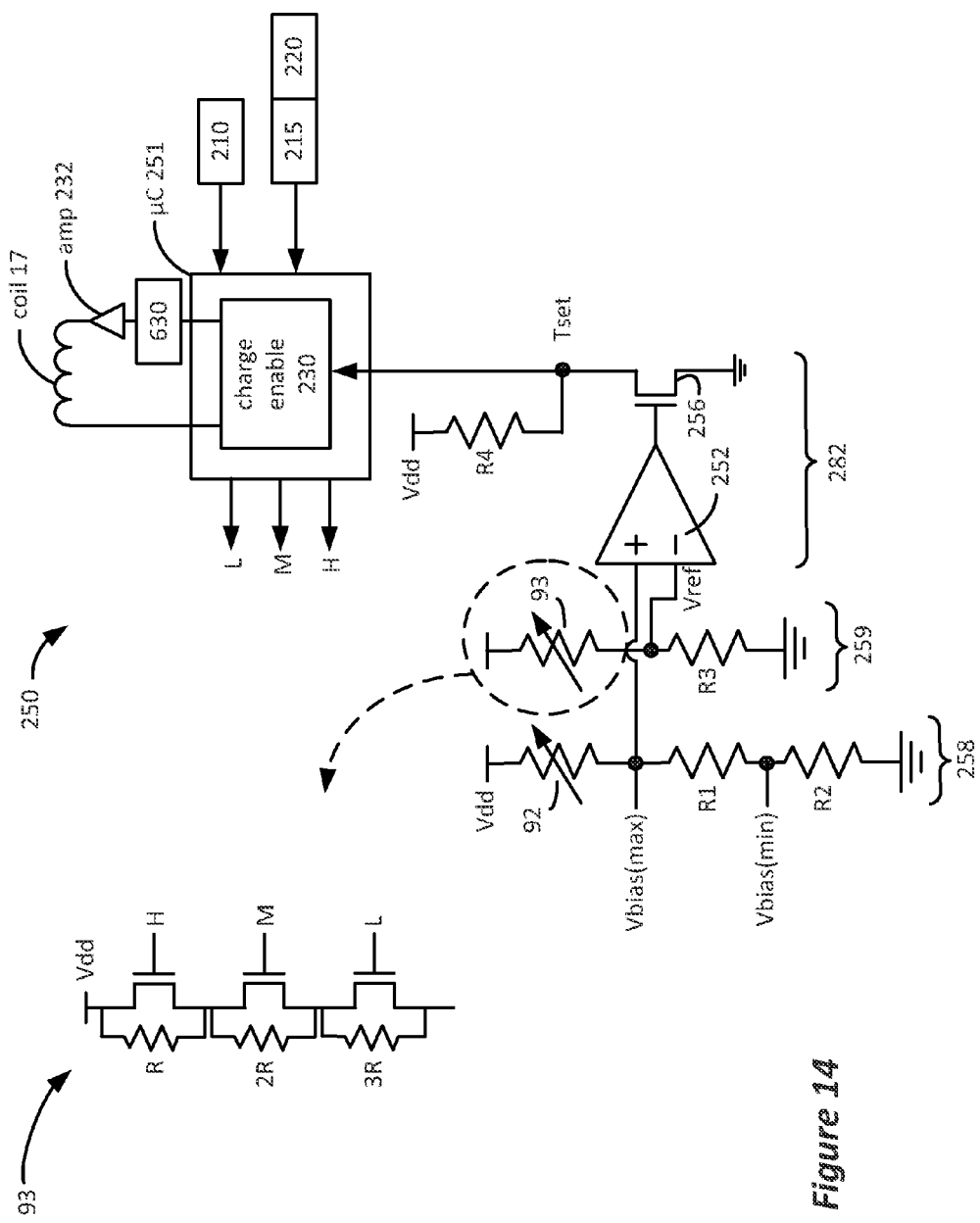
FIG. 14 illustrates a schematic of the temperature monitoring and control circuitry for another embodiment of an external charger.
Figure 15:
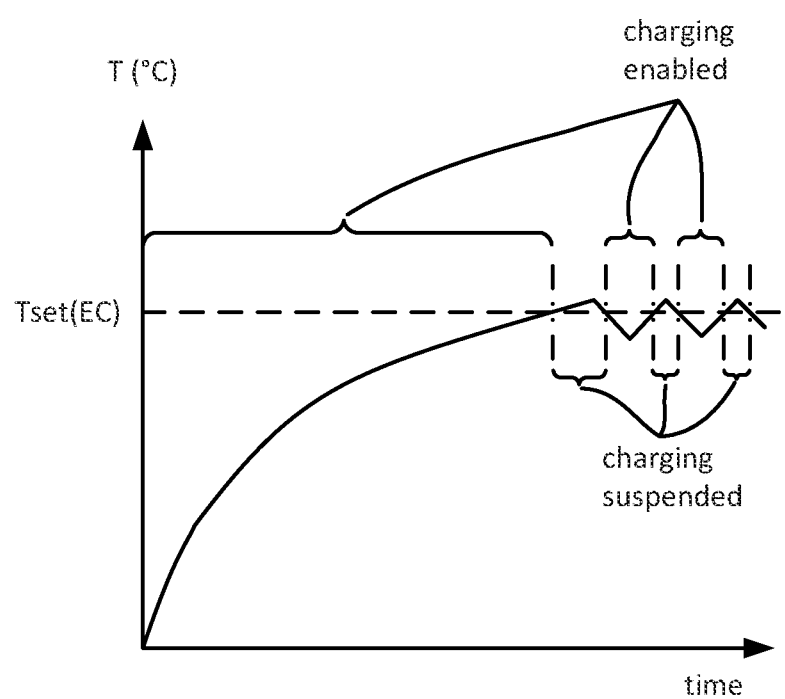
FIGS. 15-17 illustrates different examples of regulation of the external charger's temperature during IPG battery charging for the embodiment of FIG. 14.

FIG. 15 illustrates operation of the temperature monitoring and control circuitry 250 of FIG. 14. When the external charger 200 exceeds Tset(EC), charging is suspended until the temperature falls below Tset(EC), at which point charging is resumed. Thus, the temperature T(EC) of the external charger 200 oscillates around the Tset(EC) value.

Figure 16:
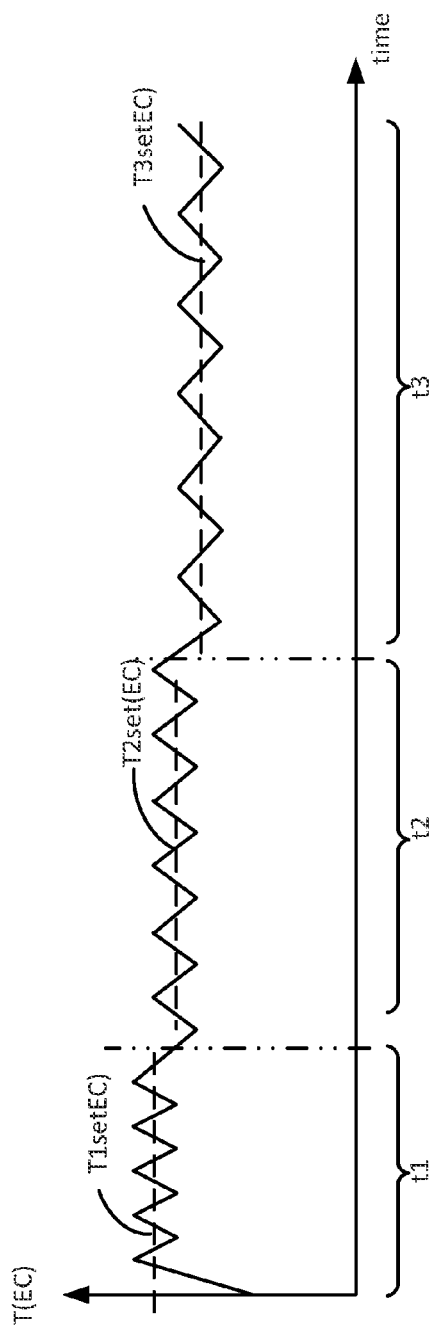
Figure 17:
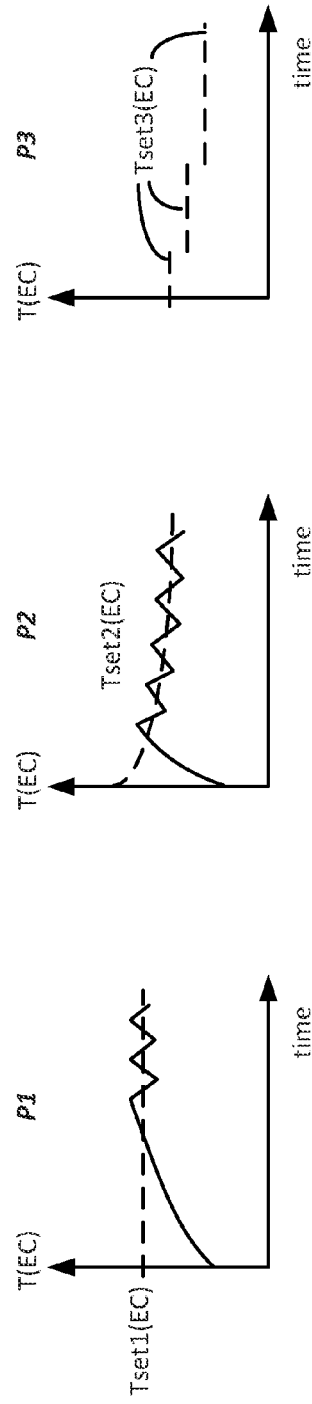

Use of a single temperature set point, Tset(EC), can also be used in conjunction with embodiments having temperature programs stored in the external charger, such as the single program example of FIGS. 8-10 and the multiple program example of FIGS. 11A-13. FIGS. 16 and 17 respectively illustrate operation of the temperature monitoring and control circuitry 250 of those program-based embodiments as modified per FIG. 14 to provide only a single control signal, Tset, to the charge enable circuitry 230.

In one embodiment, the external charger 200 suspends charging after a charging session of four hours of charging, or whenever the IPG 100 indicates by back telemetry that the IPG 100 is fully charged. This maximum length for a charging session can alternatively be made adjustable by the patient, using the external charger's user interface for example. If the suspension occurs before the IPG 100 is completely charged, the external charger can indicate via the user interface that the charging was incomplete, as a reminder to the patient to continue charging later.

Figure 18:
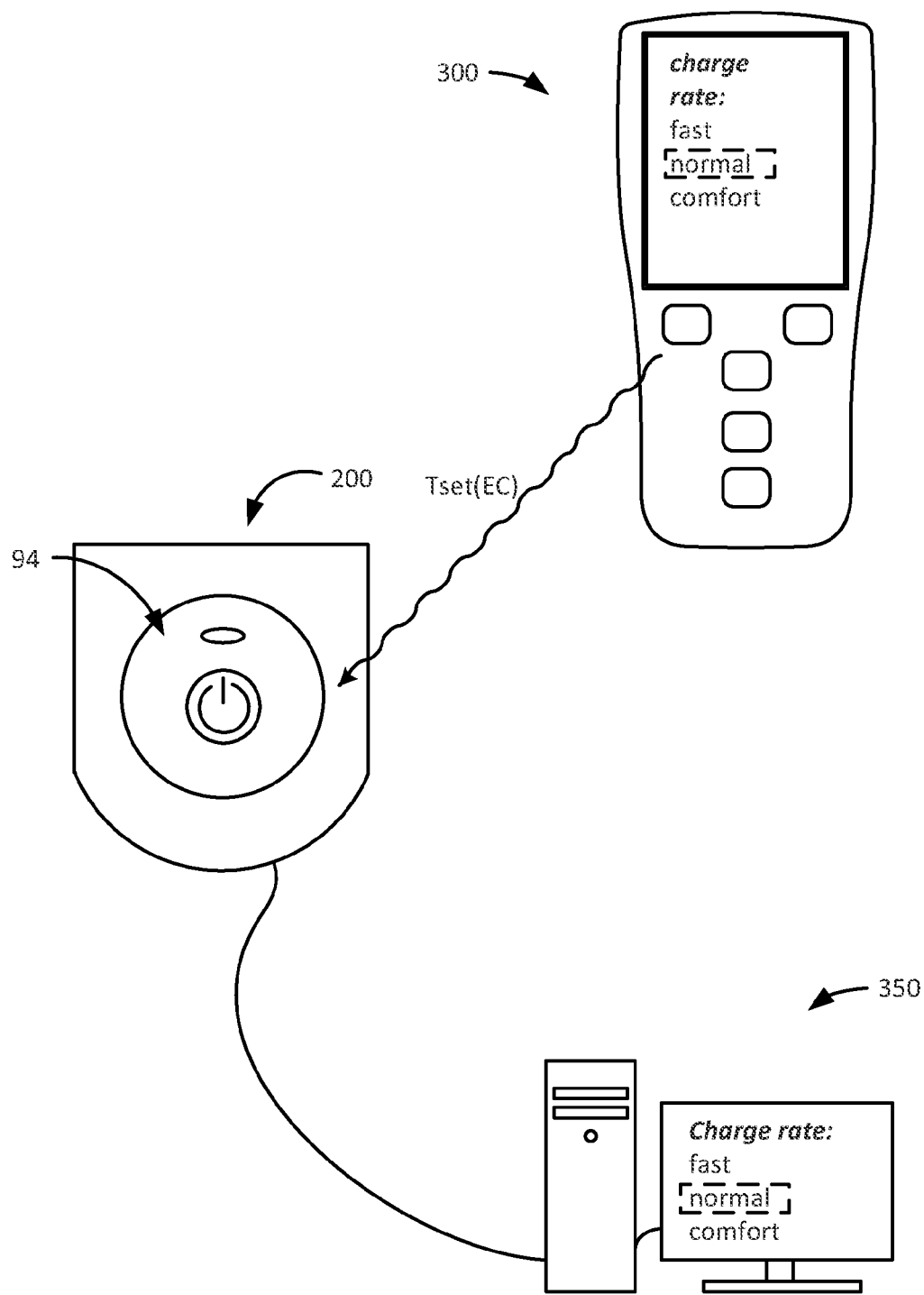
FIG. 18 illustrates programming the temperature setting of an external charger using the user interface of a different device such as an external controller or a computer.

In embodiments described to this point, the programming of the Tmax(EC)/Tmin(EC) or Tset(EC) temperatures into the improved external charger 200 occurs by use of a user interface on the external charger 200. However, this is not strictly necessary. For example, in FIG. 18, the relevant user interface appears on an external controller 300, which is traditionally used by the patient to control the implant's therapy settings. In the example shown, the external controller 300's user interface comprises a display and buttons, and is thus similar to the user interface of FIG. 5B described earlier. Once the charging rate/temperature setting is entered into the external controller 300, it can be wirelessly transmitted to the external charger 200 and stored in its memory 275 (FIG. 6A). Such wireless transmission may comprise a short-range communication link such as Bluetooth for example, as described in further detail in U.S. patent application Ser. No. 12/476,523, filed Jun. 2, 2009, which is incorporated herein by reference. Alternatively, the charging intensity/temperature can be programmed into the external charger 200 by using a wired connection to the patient's or clinician's computer 350 for example. In either case, the patient's ability to program the temperature after manufacture is preserved.

Although it is envisioned that the disclosed external chargers 200 would normally be used to charge a battery 26 within the IPG 100, the external charger 200 can also be used with IPGs or other implantable medical devices that lack a battery. This could occur for example in a system in which the IPG continually wirelessly receives energy from the external charger 200, which IPG in turn rectifies and uses this energy without storage.

Although in a preferred embodiment the external charger 200 employs a thermistor, other temperature sensors devices may be used, such as thermocouples, resistance temperature detectors (RTDs), semiconductor junction circuits, and/or circuits employing such devices.

The various examples of temperature monitoring and control circuitry 250 are used to enable or disable charging in conjunction with consideration of the set points Tmax(EC)/Tmin(EC) or Tset(EC). However, such enabling or disabling of the external charger is not strictly required to control the external charger 200's temperature. For example, instead of completely disabling the external charger 200 when Tmax (EC) is exceeded, the charge enable circuitry 230 (FIG. 6A) could instead reduce the current flow through the charging coil 17, instead of curtailing it altogether. Alternatively, the charge enable circuitry 230 could start to duty cycle current to the coil 17. In short, there are many different ways the power output of the external charger 200 could be controlled to keep the external charger's temperature in line with the temperature set points disclosed herein, and the disclosed techniques are not limited to the embodiments illustrated.

Furthermore, although the embodiments described above provide for a user interface to allow a patient to program the external charger 200, in other embodiments, the user interface can be omitted, allowing for programming the external charger 200 only by the factory. Alternatively, a clinician interface can be provided to allow a clinician to program the external charger 200, even if the external charger 200 has no user interface for patient programming of the external charger 200.

Use of the term "programming" should not be interpreted as requiring the ability to program software that controls the external charger 200, but should be understood to include any technique for controlling or modifying the functionality of the external charger 200 to modify its operating characteristics, such as maximum temperature settings, including hardware and circuitry techniques for accomplishing such control or modification.

In summary, an external charger 200 permits a patient to control the maximum temperature of the external charger 200 while charging. This controlled temperature regulation can provide faster charging with improved comfort and safety.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

I claim:

1. An external charger for use with an implantable medical device, comprising:
    a coil configured to produce energy receivable by the implantable medical device to power or charge the implantable medical device during a charging session;
    temperature monitoring and control circuitry configured to detect a temperature of the external charger and to control activation of the coil in accordance with a temperature set point; and
    memory comprising a plurality of selectable temperature programs, wherein each temperature program comprises at least one temperature set point, wherein the memory is configured to provide the at least one temperature set point of a selected temperature program to the temperature monitoring and control circuitry during the charging session.

2. The external charger of claim 1, further comprising a user interface configured to allow a user to select the selected temperature program.

3. The external charger of claim 2, wherein the user interface comprises a screen.

4. The external charger of claim 2, wherein the user interface is further configured to store the temperature programs in the memory.

5. The external charger of claim 1, wherein the memory is contained within a microcontroller.

6. The external charger of claim 1, wherein the temperature monitoring and control circuitry controls activation of the coil by adjusting a charging current through the coil.

7. The external charger of claim 1, wherein the temperature monitoring and control circuitry controls activation of the coil by duty cycling a charging current through the coil.

8. The external charger of claim 1, wherein the temperature monitoring and control circuitry disables activation of the coil after a predetermined charging time.

9. The external charger of claim 1, wherein at least one of the temperature programs comprises a plurality of different temperature set points.

10. The external charger of claim 1, wherein at least one of the temperature programs comprises a plurality of different temperature set points and a plurality of times at which the temperature set points are provided to the temperature monitoring and control circuitry during the charging session.

11. The external charger of claim 10, wherein the temperature set points provided to the temperature monitoring and control circuitry decrease during the charging session.

12. The external charger of claim 1, wherein at least one of the temperature programs comprises a temperature set point that automatically varies during the charging session.

13. The external charger of claim 12, wherein the temperature set point decreases during the charging session.

14. An external charger for use with an implantable medical device, comprising:
    a coil, wherein the coil is selectively activated to produce energy receivable by the implantable medical device to power or charge the implantable medical device during a charging session;
    a temperature-sensitive element for detecting the temperature of the external charger;

control circuitry configured to duty cycle or reduce a charging current through the coil when the external charger temperature during the charging session is above a temperature set point; and memory comprising a plurality of selectable temperature programs, wherein each temperature program comprises at least one temperature set point, wherein the memory is configured to provide the at least one temperature set point of a selected temperature program to the control circuitry during the charging session.

15. The external charger of claim 14, further comprising a user interface configured to allow a user to select the temperature program.

16. The external charger of claim 15, wherein the user interface comprises a screen.

17. The external charger of claim 14, wherein the memory is contained within a microcontroller.

18. The external charger of claim 14, wherein the control circuitry disables activation of the coil after a predetermined charging time.

19. The external charger of claim 14, wherein at least one of the temperature programs comprises a plurality of different temperature set points.

20. The external charger of claim 14, wherein at least one of the temperature programs comprises a plurality of different temperature set points and a plurality of times at which the temperature set points are provided to the control circuitry during the charging session.

21. The external charger of claim 20, wherein the temperature set points provided to the control circuitry decrease during the charging session.

22. The external charger of claim 14, wherein at least one of the temperature programs comprises a temperature set point that automatically varies during the charging session.

23. The external charger of claim 22, wherein the temperature set point decreases during the charging session.

* * * * *